US00PP10584P

United States Patent [19]

Grueber

[11] Patent Number: Plant 10,584

[45] Date of Patent: Sep. 1, 1998

[54] SCAEVOLA PLANT NAMED 'NEWON'

[75] Inventor: Garry Henry Grueber, Mainz, Germany

[73] Assignee: Innovaplant GmbH & Co. KG, Gensingen, Germany

[21] Appl. No.: 715,504

[22] Filed: Sep. 18, 1996

[51] Int. Cl.[6] ..... A01H 5/00

[52] U.S. Cl. ..... Plt./68.1

[58] Field of Search ..... Plt./68.1

[56] References Cited

U.S. PATENT DOCUMENTS

P.P. 7,929 8/1992 Rother ..... Plt./68.1

OTHER PUBLICATIONS

UPOVROM 1997/01 Disk Search Report ① PBR 02417, 1997.

UPOVROM Disk 1997/01 Search Report ② PBR 12500002, 1997.

UPOVROM Disk 1997/01 Search Report ③ PBR 001614, 1997.

UPVOROM Disk 1997/01 Search Report ④ PBR SVL 0002, 1997.

*Primary Examiner*—Howard J. Locker
*Assistant Examiner*—Kent L. Bell
*Attorney, Agent, or Firm*—C. A. Whealy

[57] ABSTRACT

A distinctive cultivar of Scaevola plant named 'Newon' characterized by its compact plant habit; dense and bushy plant form; freely branching plant habit; early to flower; and violet blue fan-shaped flowers.

3 Drawing Sheets

The present invention relates to a new and distinct cultivar of Scaevola plant, botanically known as *Scaevola aemula* and referred to by the cultivar name 'Newon'.

The new cultivar is a product of a planned breeding program conducted by the inventor in Gensingen, Germany. The objective of the breeding program was to develop compact freely-branching cultivars that flower quickly.

The new cultivar originated from a cross made by the inventor in 1990 of an unidentified seedling selection of *Scaevola aemula*, as the male or pollen parent, with the *Scaveola aemula* cultivar Blue Wonder (disclosed in U.S. Plant Pat. No. 7,929), as the female or seed parent. The cultivar Newon was discovered and selected by the inventor as a flowering plant within the progeny of the stated cross in a controlled environment in Genisingen, Germany.

Asexual reproduction of the new cultivar by terminal cuttings taken in Gensingen, Germany, has shown that the unique features of this new Scaevola are stable and are reproduced true to type in successive propagations.

The new cultivar has not been observed under all possible environmental conditions. The phenotype may vary somewhat with variations in environment such as temperature, daylength and light intensity, without, however, any variance in genotype.

Plants of the new Scaevola differ from plants of the parent cultivar 'Blue Wonder' in the following characteristics:

1. Plants of the new Scaevola flower about one week earlier than plants of the cultivar 'Blue Wonder'.
2. Plants of the new Scaveola have smaller, less dentated leaves compared to plants of the cultivar 'Blue Wonder'.
3. Plants of the new Scaveola are less open and outwardly spreading and have a denser, bushier plant habit and are more freely branching than plants of the cultivar 'Blue Wonder'.
4. Plants of the new Scaevola have shorter peduncles than plants of the cultivar 'Blue Wonder'.
5. Plants of the new Scaevola have more resistance to plant diseases such as Pythium and Verticillium than plants of the cultivar 'Blue Wonder'.

The following characteristics have been repeatedly observed and are determined to be basic characteristics of 'Newon' which distinguish 'Newon' as a new and distinct cultivar:

1. Compact plant habit.

2. Dense and bushy plant form and freely branching plant habit.
3. Early flowering.
4. Violet blue fan-shaped flowers.

The accompanying colored photographs illustrate the overall appearance of the new cultivar, showing the colors as true as it is reasonably possible to obtain in colored reproductions of this type.

The first photograph comprises a side perspective view of a typical hanging basket plant of 'Newon'.

The second photograph comprises a close-up view of flowers of plants of 'Newon'.

The third photograph comprises a top perspective view of typical young hanging baskets of the cultivar 'Blue Wonder' (left) and the cultivar Newon (right).

Perianth coloration of the photograph on sheet 1 closely approximates the actual perianth color. Perianth coloration of the photographs on sheets 2 and 3 appears pink rather than the actual violet blue perianth color due to light reflectance.

The following observations, measurements, values and comparisons describe plants grown in Encinitas, Calif., under outdoor conditions Color references are made to The Royal Horticultural Society Colour Chart except where general terms of ordinary dictionary significance are used.

Botanical classification: *Scaevola aemula* cultivar 'Newon'.

Parentage:

*Male or pollen parent.*—Unidentified seedling selection of *Scaevola aemula*.

*Female or seed parent.*—*Scaevola aemula* cultivar 'Blue Wonder', U.S. Plant Pat. No. 7,929.

Propagation:

*Type cutting.*—Terminal cuttings.

*Time to initiate and develop roots.*—Summer: About 21 days at temperatures of 22° C. Winter: About 28 days at temperatures of 20° C.

*Rooting habit.*—Numerous, fibrous, and freely branching.

Plant description:

*Plant form.*—Initially upright, then as stems elongate, spreading. Suitable for hanging basket containers.

*Growth habit.*—Moderately vigorous and freely branching, dense and bushy.

*Stem description.*—Aspect: Upright initially, then spreading as stems elongate. Internode length: About 15 mm. Diameter: About 5 mm. Color: 144A, young shoots with anthocyanin, 59A. Texture: Smooth, glabrous.

*Foliage description.*—Arrangement: Alternate, single. Size: Length: 6 to 7.5 cm. Width: 2 to 2.5 cm. Shape:Spatulate. Tip: Acute. Base: Attenuate. Margin: Immature: Entire. Fully expanded: Irregulary serrated, becoming more serrated toward leaf tip. Texture: Glabrous, coarse, not smooth. Color: Immature: Upper surface: 137A. Lower surface: 147B. Fully expanded: Upper surface: 137A. Lower surface: 147B.

Flower description:

*Flower type and shape.*—Semi-circular, fan-shaped flowers with five petals fused at the base to form a tubular flower throat. Flower throat open along the upper surface exposing reproductive organs. Flowers persistent.

*Flower arrangement.*—Flowers arise from leaf axils with one flower per axil.

*Perianth.*—Aspect: Fan-shaped, flat. Diameter: 2.5 to 3 cm. Venation: Parallel. Color: Upper surface: Violet-blue, 90B, fading to 91A with age. Lower surface: Violet-blue, 90C, fading to 91A with age. Venation: Darker violet-blue, 90A.

*Petals.*—Quantity: Five. Shape: Oblanceolate. Tips: Mucronate.

*Flower throat.*—Length: About 15 cm. Diameter: About 4 mm. Color: Throat opening: Base of petals are white where fused with two bright yellow stripes, 6A, and purple, 90A, venation. Lower surface: 145A.

*Sepals.*—Quantity: Two. Shape: Linear. Size: Length: About 10 mm. Width: About 1.5 mm. Color: 137A.

*Reproductive organs.*—Gynoecium: Ovary: Shape: Elongate. Length: 1 to 2 mm. Color: Light green. Style: Length: About 1.4 cm. Color: Distal end, 59A, proximal, 144B. Stigma: Appearance: Deltoid with purplish hairs 2 mm in length. Aspect: Bent at a 90° angle to style. Androecium: Filaments: Quantity: 5. Length: About 5 mm. Color: Initially white and becoming dark purple with development. Anthers: Length: About 1 mm. Color: Initially white and becoming dark purple with development.

Disease resistance: More resistant to plant diseases than plants of the cultivar 'Blue Wonder'.

Seed production: Seed production is generally not observed.

It is claimed:

1. A new and distinct Scaevola plant named 'Newon', as illustrated and described.

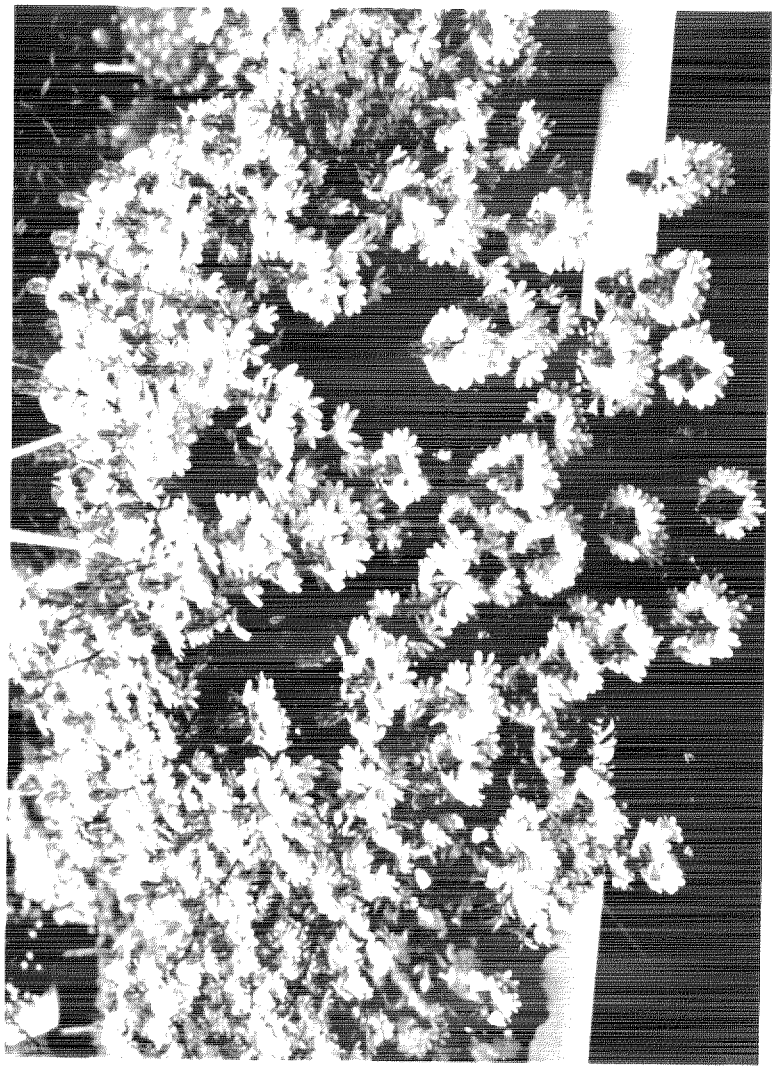

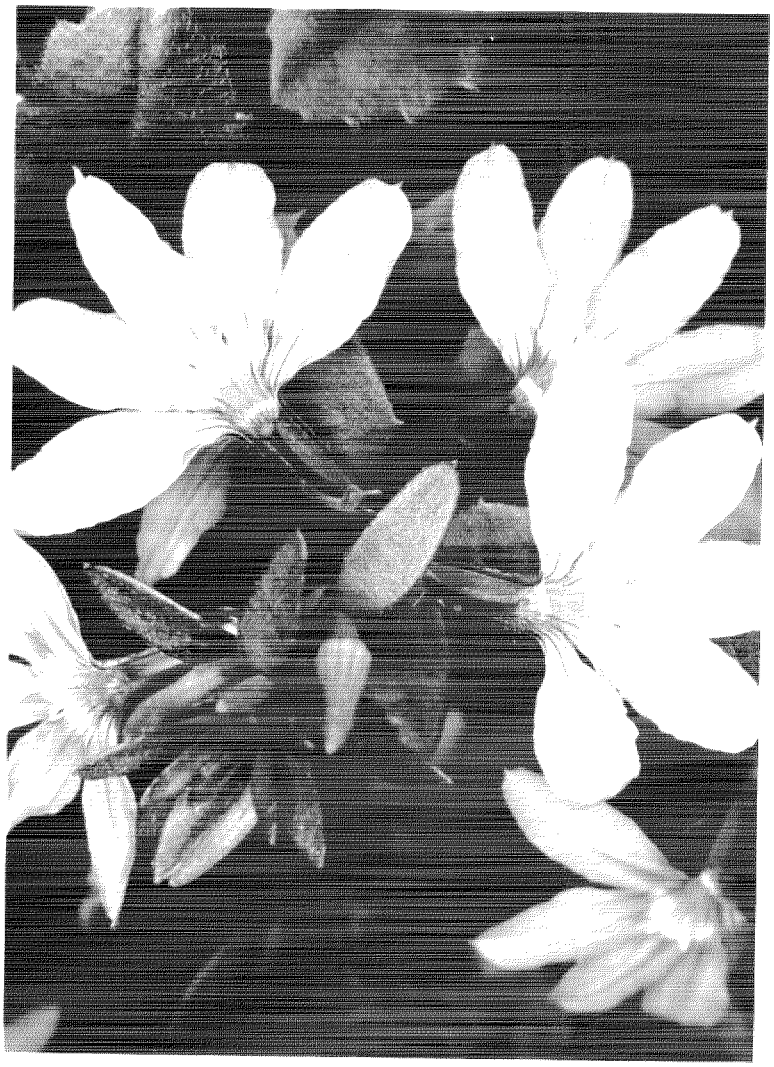

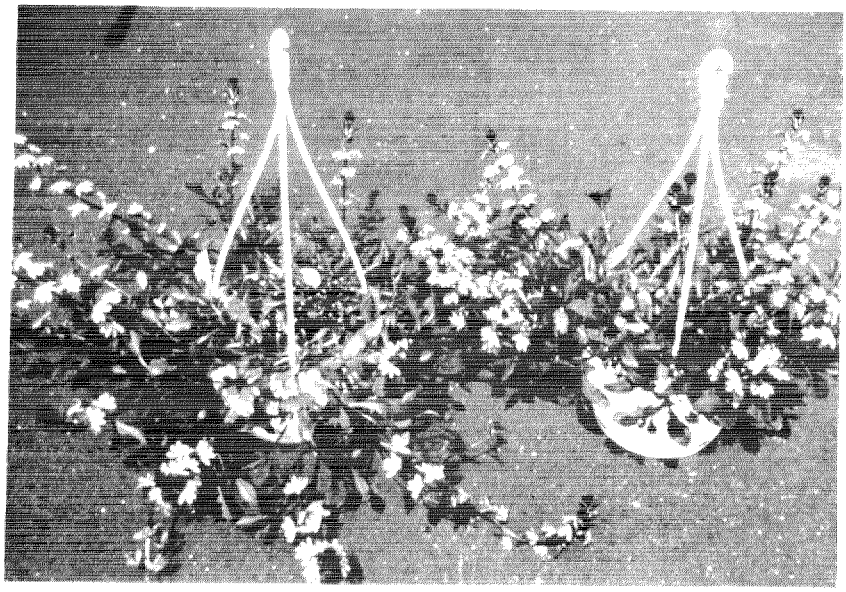

* * * * *